(12) United States Patent
Husted

(10) Patent No.: US 7,055,530 B2
(45) Date of Patent: Jun. 6, 2006

(54) DENTAL CLEANING STRIP

(75) Inventor: Eston A. Husted, St. Paul, MN (US)

(73) Assignee: Mardelle M. LaMoure, St. Paul, MN (US)

(*) Notice: Subject to any disclaimer, the term of this patent is extended or adjusted under 35 U.S.C. 154(b) by 93 days.

(21) Appl. No.: 10/458,587

(22) Filed: Jun. 10, 2003

(65) Prior Publication Data
US 2004/0163664 A1 Aug. 26, 2004

Related U.S. Application Data

(60) Provisional application No. 60/450,017, filed on Feb. 25, 2003.

(51) Int. Cl.
A61C 15/00 (2006.01)

(52) U.S. Cl. .................................... 132/321

(58) Field of Classification Search ................ 132/321, 132/329; 401/142, 125, 166
See application file for complete search history.

(56) References Cited

U.S. PATENT DOCUMENTS

| 1,637,153 | A | * | 7/1927 | Lawton ........................ 401/34 |
| 3,511,249 | A | * | 5/1970 | Baitz ........................... 132/329 |
| 3,754,332 | A | * | 8/1973 | Warren, Jr. ............... 433/217.1 |
| 3,943,949 | A |   | 3/1976 | Ashton et al. |
| 4,033,365 | A |   | 7/1977 | Klepak et al. |
| 4,270,556 | A |   | 6/1981 | McAllister |
| 4,414,990 | A |   | 11/1983 | Yost |
| 4,450,849 | A | * | 5/1984 | Cerceo et al. ............... 132/321 |
| 4,583,564 | A |   | 4/1986 | Finkelstein et al. |
| 4,646,766 | A |   | 3/1987 | Stallard |
| 4,776,358 | A | * | 10/1988 | Lorch .......................... 132/321 |
| 4,974,615 | A |   | 12/1990 | Doundoulakis |
| 5,220,932 | A |   | 6/1993 | Blass |
| 5,518,012 | A |   | 5/1996 | Dolan et al. |
| 5,692,530 | A |   | 12/1997 | Bible et al. |
| 5,765,576 | A |   | 6/1998 | Dolan et al. |
| 5,848,600 | A |   | 12/1998 | Bacino et al. |
| 5,878,758 | A |   | 3/1999 | Bacino et al. |
| 5,927,299 | A |   | 7/1999 | Rappoport |
| 5,967,154 | A | * | 10/1999 | Anderson ..................... 132/321 |
| 6,251,410 | B1 |   | 6/2001 | Schiraldi et al. |
| 6,508,649 | B1 | * | 1/2003 | Gratz .......................... 433/142 |

* cited by examiner

Primary Examiner—John J. Wilson
Assistant Examiner—Robyn Doan
(74) Attorney, Agent, or Firm—Anthony G. Eggink; Katrina M. Eggink

(57) ABSTRACT

A flexible strip of a polymeric material having a plurality of apertures with raised peripheral portions for use to remove plaque, debris, and stains from interproximal surfaces and contact areas of the teeth without damaging tooth enamel. The polymeric material may be formed into apertured strips by means of a laser. The flexible strips have raised edges and raised peripheral shapes extending from both sides of the strip.

12 Claims, 4 Drawing Sheets

DENTAL CLEANING STRIP

This application claims the benefit of U.S. Provisional Patent Application No. 60/450,017, filed on Feb. 25, 2003.

BACKGROUND OF THE INVENTION

This invention relates generally to devices for cleaning teeth and a process for making such cleaning devices. Particularly, this invention relates to a flexible polymeric dental cleaning strip usable by consumers to clean the interproximal areas between the teeth.

Various devices and techniques are used by individuals for teeth cleaning purposes. An individual typically uses a tooth brush with toothpaste which may contain abrasive materials, to clean the exterior surfaces of the teeth. For cleaning the interproximal or areas between the teeth, dental floss has usually been utilized. Dental floss which is marketed in many forms and configurations may comprise a string material such as cotton or other materials of a specified diameter or thickness. Dental floss is manipulated between the teeth to aid in cleaning and removing debris between the teeth and at the gum line. Dental floss, however, is typically too soft to effectively remove tartar, calcified plaque and other stain material from tooth surfaces. Dentists and dental hygienists are consulted to remove the latter using various scaling tools and other methods. The consumer, therefore, is limited to the tools, i.e., tooth brushes and floss, and techniques available in the marketplace for cleaning teeth.

The dental strips of the present invention are designed for consumer use and have ridged apertures and edges which permit the strips to be used between the teeth and against the gum line. The dental strips permit the consumer to clean teeth beyond presently known devices. The flexible apertured strips overcome the limitations of prior art teeth cleaning devices.

It is the purpose of the present invention to provide a flexible polymeric cleaning strip, i.e., constructed of a nylon material or the like, having a plurality of apertures with raised peripheries preferably disposed on both opposing strip surfaces. The cleaning strip may be inserted between the teeth and used in a manner similar to dental floss. The dental cleaning strip of the invention may be provided in a variety of configurations, each being constructed and arranged to provide the consumer with an easy and effective means to clean and care for teeth. The dental cleaning strips may also be provided with coatings and agents which may be released for transfer during teeth cleaning procedures.

SUMMARY OF THE INVENTION

This invention comprises a flexible polymeric strip having raised side edges and having a plurality of apertures with raised peripheral edges for engaging and cleaning the teeth of a user. The raised edges are formed around each aperture and extend outwardly on at least one lateral surface of the strip so that the strip may clean both teeth when used manipulated during use.

The dental cleaning strip is preferably constructed of a flexible polymeric material, such as nylon or the like and which is softer than tooth enamel. Tooth enamel hardness has been found to be approximately Brinell 350. The flexible polymeric material of the present invention has a hardness less than the hardness of tooth enamel. However, the hardness of the polymeric material may be controlled and may exceed the cleaning action of typical dental floss.

The present invention further relates to a polymeric dental cleaning strip which is shaped and configured utilizing a melting process. The melting process, for example, may utilize a laser process wherein individual laser beams are directed at a length of polymeric material or a moving polymeric web (a moving length of polymeric roll stock material, i.e., nylon or the like) which shape the strip, the strip edges and the location, shape and the peripheral structural outline of the holes, lines or aperture pattern of the polymeric strip material. The melting process may be controlled by the physical and thermal properties of the selected polymer, such as thickness, melting point as well as the type of laser and laser beam controls of the laser beam assembly. Although the use of lasers are discussed herein, other melting means and processes may be utilized to practice the processes and making the cleaning strip devices of this invention.

The dental cleaning strips of the invention may be colored, printed, coated and shaped to provide various dental cleaning benefits. For example, the strips may be colored, i.e., blue or be printed for identifying a specific product type directed to specified uses, i.e., consumer type, thickness and cleaning ability. Coatings and/or agents may be provided on the strip surfaces or captured in the apertures for medical and dental benefits. The dental strips may also have widened or thickened strip portions for ease of dental strip use.

In addition to surface coatings, materials or agents may be imbedded or captured within individual apertures so as to be dispersed or released onto the interproximal areas automatically as the user causes the apertures to pass between the teeth. The transferred materials may be dissolvable by saliva, for example.

The coatings and release agents used in connection with the dental cleaning strips of the invention provide a "put and take" effect whereby cleaning agents and the like are placed onto and between the teeth while debris and plaque are taken away via the ridged apertures and side edges of the device.

The dental cleaning strips of the invention may be provided in roll or strip form, and may have different cleaning properties on the opposing strip surfaces. A laser process may be utilized to control the various physical properties of the cleaning strip.

These and other benefits of this invention will become apparent from the following description by reference to the drawings.

DESCRIPTION OF THE PREFERRED EMBODIMENTS

Figure 1:
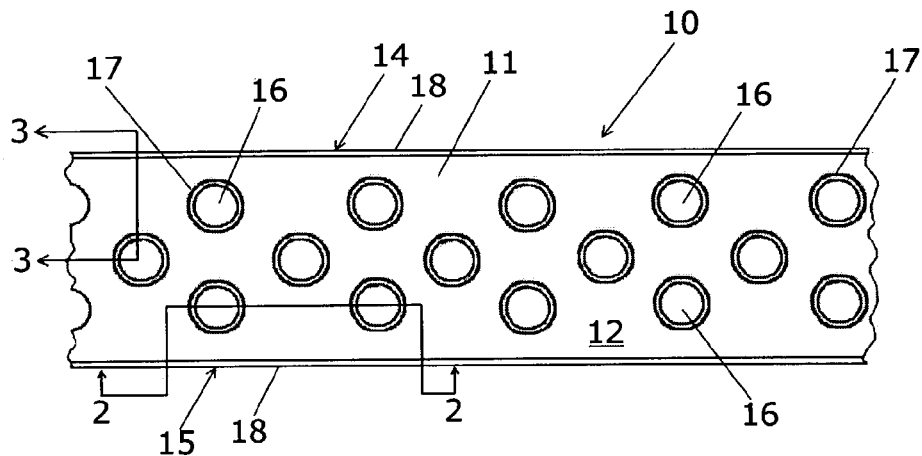
FIG. 1 is a top plan view of a length of the dental cleaning strip of the present invention.
Figure 2:
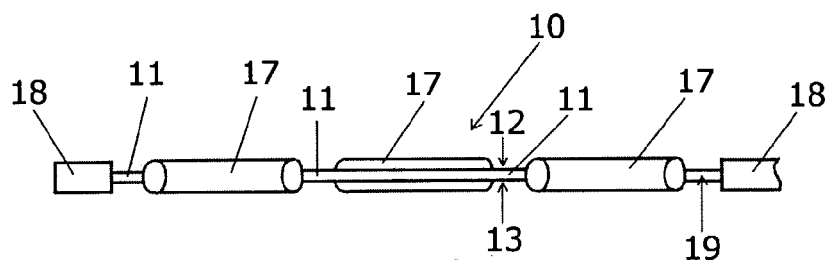
FIG. 2 is a sectional view of the dental cleaning strip taken along lines 2—2 of FIG. 1.
Figure 3:
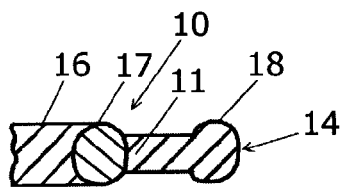
FIG. 3 is a sectional view of the dental cleaning strip taken along lines 3—3 of FIG. 1.

Referring to FIGS. 1–3, the dental strip 10 of the invention is shown comprised of an elongated strip body 11 having opposing surfaces 12 and 13. The strip body 11 is flexible, has side edges 14 and 15 and a pattern of holes or apertures 16. Importantly, the side edges 14 and 15 are shown to have raised edges 18 and each aperture 16 has a raised ridge 17 thereabout. The strip body 11 has a thickness 19 and the raised edges 18 as well as the raised ridges 17 defining each aperture 16 extend upward and downward whereby both opposing surfaces 12 and 13 have predetermined elevated or raised areas.

The strip body 11 of the invention is preferably constructed of a polymeric material which is strong and flexible so that it may be manipulated between the teeth of a user. For example, nylon has been found suitable, although any flexible polymeric material may be used within the purview of the present invention. Other flexible polymeric materials and laminations may be used to create the dental cleaning strips, i.e., polyesters, polypropylene, polyethylene and plastic materials used in the medical and packaging fields, and the like.

Figure 4:
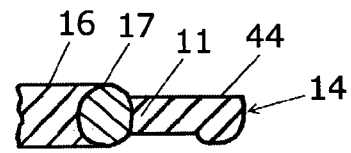
FIG. 4 is a sectional view of another embodiment of the dental cleaning strip of the invention.

FIG. 3 is a sectional view showing the raised edge 18 and the peripheral ridge 17 about the aperture 16 with respect to the relative thickness of the strip body 11. FIG. 4 is another embodiment of edge 14 wherein the thickened or raised edge portion 44 is shown to extend from one surface of strip body 11. It is within the purview of this invention to provide dental cleaning strips having raised edges 18 and/or peripheral ridges 17 which extend from one or both sides of the strip body 11. Thus, the strip body may have only raised edges 18, only peripheral ridges 17 or both and having the edges 18 and ridges 17 either extending from one or both sides of the strip body 11, or with any combination thereof.

Figure 5:
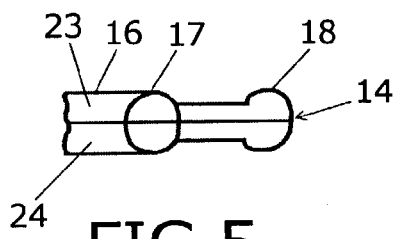
FIG. 5 is a sectional view of another embodiment of the dental cleaning strip of the invention.
Figure 6:
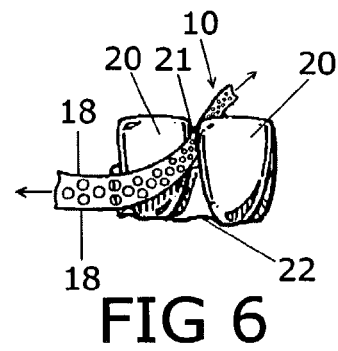
FIG. 6 is a frontal plan view showing the dental cleaning strip used on the teeth of a user.

FIG. 5 shows that the strip body may be constructed of two or more laminated materials, i.e., polymeric layers 23 and 24. As will be further discussed below the different plastic materials 23 and 24 may have different properties, i.e., melting points and hardness, whereby the effect of the dental strip formed of such materials may exhibit or provide different teeth cleaning results. Various additives may also be provided in the polymer, i.e., metallic compounds, to thereby control the thickness and hardness of the cleaning edges and aperture peripheries. FIG. 6 shows the dental strip 10 used, like floss between teeth 20, to clean the interproximal surface 21 and whereby the dental strip 10 is moved in a back and forth motion. Further, because of the raised edges 18 of the dental cleaning strip 10, the strip of this invention may be utilized adjacent to the gum line 22.

The polymeric dental cleaning strip material 11 may be a flexible film made of nylon 6,6, for example Dartek® C-917 a DuPont nylon film sold by Enhance Packaging Technologies, Inc., for example. This nylon film may be thermoformed, printed, laminated or coated. The film may be provided in thickness of 0.60, 0.75, 1.00, 1.25, 1.50, 2.00, 2.50, 3.00, 4.00 mils, has a melting point of 510° F., has a smooth, uniform surface, has toughness, thin gauge and clarity. These films may be provided in other thicknesses and are typically provided in roll form, however, specified lengths of polymeric materials may also be utilized to form the dental cleaning strips of this invention.

Figure 7:
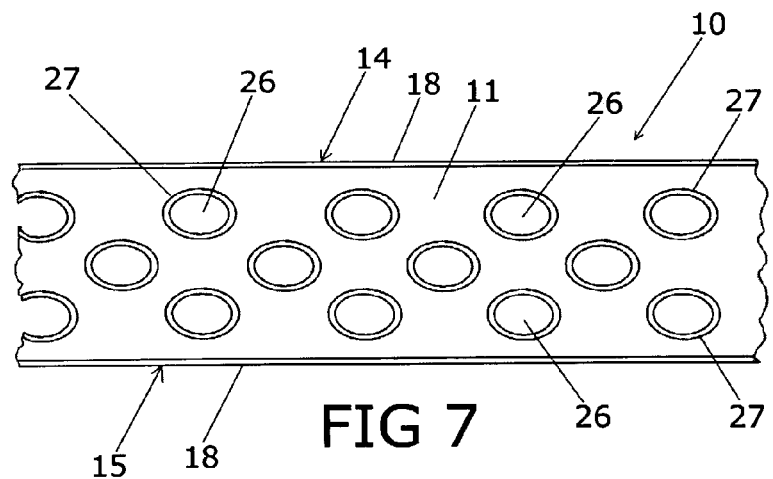
FIG. 7 is a top plan view showing another embodiment of the invention.

Referring to FIGS. 1 and 7, the dental cleaning strip 10 may utilize differently sized and shaped apertures. For example, FIG. 7 shows a pattern of oval shaped apertures 26, each having a peripheral ridge 27. Although the aperture patterns shown in FIGS. 1 and 7 are each comprised of three rows of apertures, other patterns, whether regular and repeating or irregular and non-repeating may be utilized within the purview of this invention.

Figure 8:
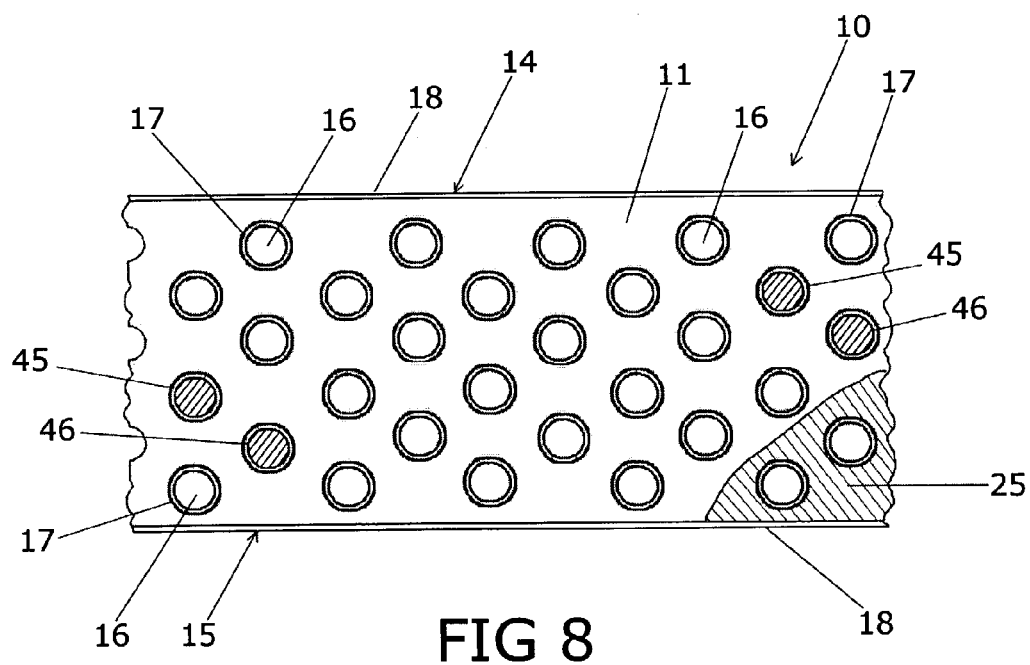
FIG. 8 is a top plan view showing another embodiment of the invention.

Referring to FIG. 8, the dental cleaning strip 10 is shown to be wider than the strips shown in FIGS. 1 and 7. Although the thickness 19 of the strip body may be varied, a wider strip as shown in FIG. 8, may be utilized to permit a user to fold over the strip body 11 to thereby increase the overall thickness and to clean teeth having larger gaps therebetween. As shown, a coating 25 is shown applied to the surface of the strip body 11. Further, materials or agents 45 and 46 are shown captured in several apertures 16 within the confines of peripheral ridges 17. For example, anti-bacterial agents to prevent tooth decay, teeth whitening agents, anti-frictional additives, bees wax, toothpaste gel or other coatings and/or agents may be applied to the surfaces of strip 10 or placed or captured within the aperture(s) of the strip. These coatings or agents are provided for use with transport and/or transfer to the teeth of the user. The coatings or agents may be activated when used, for example by dissolving due to saliva. Further, specified widths of the cleaning strips may be provided to veterinarians to clean the teeth of animals.

Figure 9:
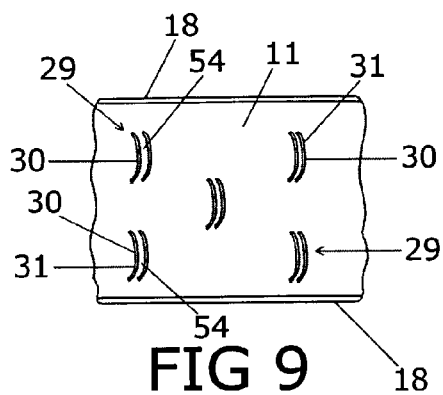
FIG. 9 is a top plan view showing another embodiment of the invention.

Referring to FIGS. 9–12, various aperture shapes and configurations are shown and which may be utilized in the dental cleaning strips of the present invention. Specifically, FIG. 9 shows a crescent slit pattern 29, each comprised of a pair of crescent slit apertures 30. Each slit aperture 30 is shown to have a raised peripheral ridge 31. As shown, the flap portion 54 created by and between the pair of slits 30 provides a flexible segment, unitary at both ends with the strip body 11, which engage the teeth of a user as the dental cleaning strip is moved between the teeth.

Figure 10:
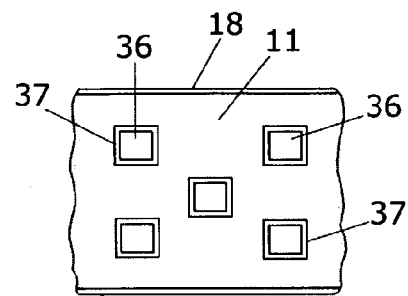
FIG. 10 is a top plan view showing another embodiment of the invention.
Figure 11:
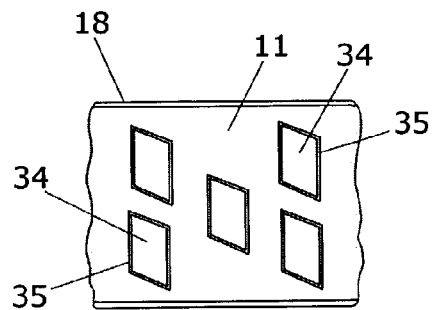
FIG. 11 is a top plan view showing another embodiment of the invention.
Figure 12:
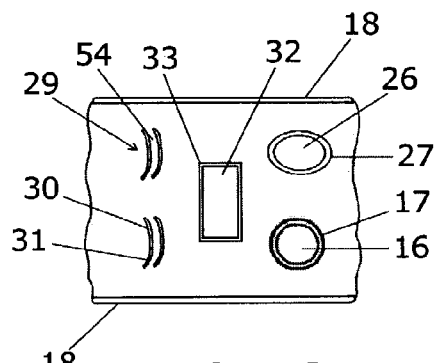
FIG. 12 is a top plan view showing another embodiment of the invention.

FIG. 10 shows a plurality of square apertures 36, each having a square peripheral ridge 37. FIG. 11 shows a plurality of trapezoidal shaped apertures 34, each having a trapezoidal shaped peripheral ridge 35. FIG. 12 shows a dental cleaning strip having a plurality of geometric shapes, namely, crescent slit patterns 29 having slits 30 and ridges 31, a rectangular aperture 32 with a peripheral rectangular ridge 33, an oval aperture 26 with a peripheral oval ridge 27 and a circular aperture 16 having a circular peripheral ridge 17. Each geometric aperture shape may have different teeth cleaning qualities and all may be utilized in a cleaning strip according to the present invention.

Figure 13:
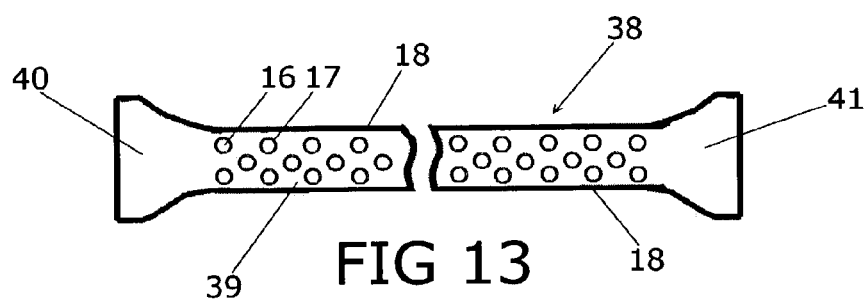
FIG. 13 is a top plan view showing another embodiment of the invention.

Referring to FIG. 13, a dental cleaning strip 38 is shown having an elongated body 39 and opposing handle member 40 and 41. The widened handles 40 and 41 are provided for users having a physical need to be able to grasp a larger strip area, i.e., the elderly, those having arthritis or other physical disabilities. Alternatively, the handle portions may have thickened portions to provide for an easier and more comfortable manipulation grip. The thickened portions may be provided by a dipping process whereby additional material is added to the strip ends. As will be further discussed, the strips of the present invention may be provided in roll form, permitting cut-off lengths as desired by the individual user or in strip form whereby each strip is provided in a predetermined length. The embodiment of FIG. 13 is suitable for the strip length style, i.e., strips of 4–12 inches.

In use, a length of a dental cleaning strip 10, i.e., 4 inches, is grasped at the ends between thumb and forefinger of each hand to provide a cleaning length of approximately one inch. After slipping the strip between the teeth, a gentle, alternating stroking motion is used to clean the teeth. Thus, the dental cleaning strips may be provided in roll form and cut off to a suitable length by the user and may be provided in predetermined strip lengths. Further, the dental cleaning strips may be provided in various colors which identify or code a specified user group or use type for example, blue—consumer; pink—children (narrower and smaller holes); heavy blue (double normal width) and other colors to identify product thickness.

Figure 14:
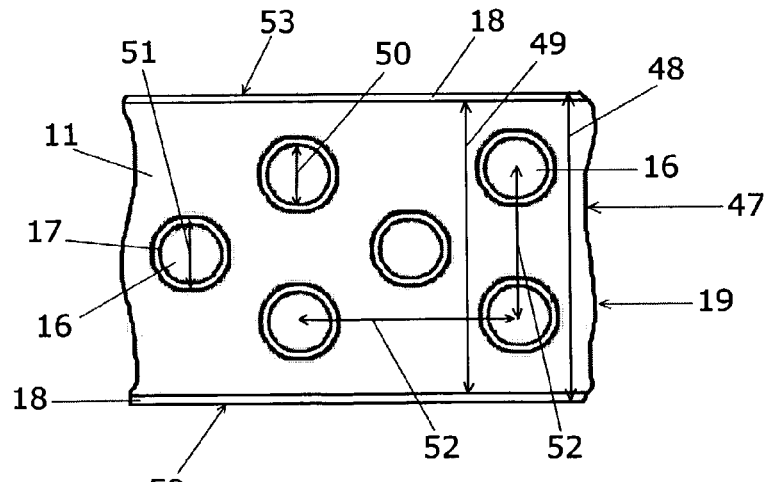
FIG. 14 is a top plan view of a length of the dental cleaning strip of the invention and showing dimensions of various elements thereof.
Figure 15:
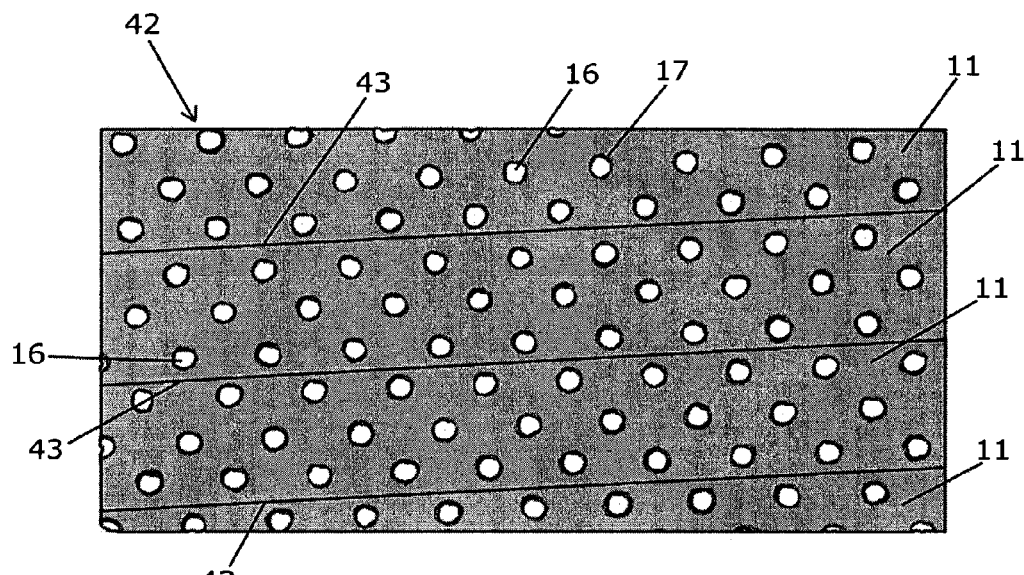
FIG. 15 is a top plan view showing a length of roll stock from which the dental cleaning strip of the invention is made.

FIG. 14 shows exemplary dimensions of a dental cleaning strip 10. These dimensions are exemplary only in that the dental strips may be provided having any specified dimensions and characteristics. For example, a dental cleaning strip 10 constructed of nylon film and having a thickness 47 of 0.003 inches has been found suitable for use according to the teachings of the present invention. As shown in FIG. 14 the strip may have an overall width 48 of approximately 0.268 inches and a width 49 of approximately 0.253 inches as measured inside the side ridges 18. The circular apertures 17 are shown to have a diameter 50 of approximately 0.042 inches and the outside diameter 51 of the peripheral ridges 17 being approximately 0.051 inches. Regarding the latter dimension 51, however, this diameter may range from 0.047–0.054 inches. The apertures 16 are shown to be spaced a distance 52 of approximately 0.136 inches, center to center in a generally square pattern, and having one such aperture 16 generally centered in the pattern. The height 53 of the side ridges 18 is shown to be approximately 0.009 inches. When the strips of this invention are produced via a laser process, as shown in FIG. 15, the tolerances may be approximately ±8.0%, for example, with respect to the side ridges, the peripheral edges as well as the aperture diameters. These variations are preferred to provide an irregular cleaning surface. However, dimension tolerances may be controlled to desired specifications.

FIG. 15 shows a photograph of a length of web stock 42 having a plurality of apertures 16. The polymeric material 42 may be provided in roll stock, run through a laser to form the apertures and to slit or cut on lines 43 to form a roll of the dental cleaning strips 10 of the present invention. The laser may also be utilized to provide strips of a specified length.

Figure 16:
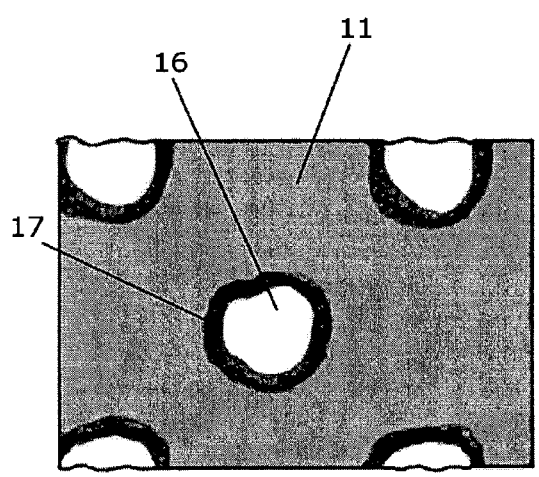
FIG. 16 shows an enlarged area of a portion of the roll stock of FIG. 14.
Figure 17:
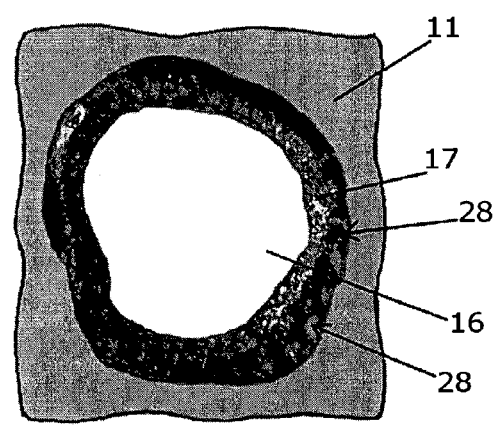
FIG. 17 is a photograph showing an enlarged peripheral ridge formed by the process of the present invention.

FIGS. 16 and 17 show enlarged views of aperture 16 in strip material 11. Particularly, the photograph shows the peripheral ridge 17 defining the aperture 16. This aperture was created via the melting process of a laser operation. Specifically, the irregular shape of the peripheral ridge 17 shows a plurality of irregular ridge portions 28 which provide the cleaning ridges of the present invention. The irregular ridge portions 28 are a series of alternating sloping surfaces which are the result of the melting and solidifying material which result from the laser process. The irregular ridge portions 28 provide an irregular peripheral cleaning ridge for cleaning and polishing of typically irregular tooth surfaces.

As many changes are possible to the dental cleaning strip embodiments and processes of this invention, utilizing the teachings thereof, the description above and the accompanying drawings should be interpreted in the illustrative and not in the limited sense.

That which is claimed is:

1. A dental cleaning strip for cleaning interproximal surfaces and contact areas between teeth, comprising a length of a unitary thin, flexible, polymeric material comprising a first polymeric layer and a second polymeric layer, said dental cleaning strip having opposing surfaces, a thickness and a plurality of spaced openings therethrough, one of said opposing surfaces having a coating disposed theron, each said opening having a raised, peripheral ridge protruding from at least one surface and being continuous about each said opening, said raised peripheral ridge having an irregular shape and irregular surfaces comprising a series of alternating sloping surfaces, at least one said opening having an agent disposed within the confines of said peripheral ridge for transfer to the teeth during use of said dental cleaning strip.

2. The dental cleaning strip of claim 1, wherein said length of polymeric material has generally parallel side edges and wherein said side edges are raised and have a thickness greater than said thickness of said polymeric material.

3. The dental cleaning strip of claim 2, wherein said raised side edges are thickened portions having irregular surfaces, said raised side edges and said peripheral ridges comprising a melted form of said polymeric material.

4. The dental cleaning strip of claim 3, wherein said openings are of a geometric shape and arranged in a predetermined pattern and wherein said geometric shape is selected from the group of shapes consisting of a circle, oval, square, rectangle, trapezoid and a crescent shape.

5. The dental cleaning strip of claim 2, wherein said raised side edge thickness and said peripheral ridge of said spaced openings are approximately the thickness of said polymeric material and wherein said raised side edge and said peripheral ridge thickness extends from each opposing surface of said polymeric material.

6. The dental cleaning strip of claim 1, wherein the polymeric material is nylon and further wherein said nylon has a predetermined color.

7. The dental cleaning strip of claim 1, wherein said polymeric material has a width of approximately 0.250 inches and wherein said openings are circular in shape, each having a diameter of approximately 0.040 to 0.050 inches.

8. The dental cleaning strip of claim 1, wherein said coating and agent is selected from the group of coatings and agents consisting of teeth whitening, antibacterial, antifrictional, toothpaste gel and bees wax compositions.

9. A dental cleaning strip for cleaning interproximal surfaces and contact areas between teeth, comprising a length of a thin, flexible, polymeric material having opposing surfaces, generally parallel side edges, a thickness and a plurality of spaced openings therethrough, each opening having a unitary raised, peripheral ridge protruding from both said opposing surfaces, wherein at least one said opening has a release agent disposed within the confines of the peripheral ridge for transfer to the teeth during use of said dental cleaning strip.

10. The dental cleaning strip of claim 9, wherein said polymeric material has a coating disposed on one said surface.

11. The dental cleaning strip of claim 10, wherein said coating and agent is selected from the group of coatings and agents consisting of teeth whitening, antibacterial, antifrictional, toothpaste gel and bees wax compositions.

12. The dental cleaning strip of claim 9, wherein said raised peripheral ridge is comprised of a melted form of said polymeric material and wherein said peripheral ridge has an irregular shape.

* * * * *